United States Patent [19]
Ramsey, III

[11] Patent Number: 5,836,895
[45] Date of Patent: Nov. 17, 1998

[54] ESOPHAGEAL CATHETER WITH GAUGE

[75] Inventor: Maynard Ramsey, III, Tampa, Fla.

[73] Assignee: Arzco Medical Systems, Inc., Tampa, Fla.

[21] Appl. No.: 370,164

[22] Filed: Jan. 9, 1995

[51] Int. Cl.$^6$ .................................................. A61B 5/103
[52] U.S. Cl. ...................... 600/593; 600/380; 600/382; 600/393
[58] Field of Search ............................ 607/124; 128/736, 128/673, 642, 675, 774

[56] References Cited

U.S. PATENT DOCUMENTS

| | | | |
|---|---|---|---|
| 4,563,176 | 1/1986 | Gustavsson et al. | 604/163 |
| 5,181,517 | 1/1993 | Hickey | 128/673 |
| 5,387,232 | 2/1995 | Trailer | 607/124 |
| 5,431,696 | 7/1995 | Atlee, III | 607/124 |
| 5,518,007 | 5/1996 | Becker | 128/774 |

OTHER PUBLICATIONS

Benson, Jr., et al., "Transesopageal Cardiac Pacing: History, Application, Technique" Clin. Prog. Pacing and Electrophysiol. vol. 2, No. 4, 1984.

Benson, Jr., "Transesophageal Electrocardiography and Cardiac Pacing: State of the Art" vol. 75 (Suppl III) Apr., 1987.

*Primary Examiner*—Max Hindenburg
*Assistant Examiner*—Pamela L. Wingood
*Attorney, Agent, or Firm*—Rockey, Milnamow & Katz, Ltd.

[57] ABSTRACT

A gauging esophageal catheter or stethoscope which is insertable into the esophagus or stomach of a subject or patient, has an elongated, flexible body portion having an instrument carried on a distal end. The catheter has a series of user visible gradations for permitting selective positioning of the instrument at a predetermined insertion depth within the subject. The gradations are calibrated to the height, weight or body surface area of the subject. The gradations may be printed on the body portion, or the body portion may have a transparent portion, and the gradations may be carried on a member internal thereto which is visible through the transparent portion.

22 Claims, 2 Drawing Sheets

ESOPHAGEAL CATHETER WITH GAUGE

FIELD OF THE INVENTION

This invention pertains to catheters inserted into the body of a subject, generally, and specifically, to esophageal catheters. More particularly, the invention pertains to gaugeable esophageal catheters which have gradations for calibrating the insertion depth into a subject, relative to the height of the subject.

BACKGROUND OF THE INVENTION

Non-invasive esophageal catheters and stethoscopes are known for use in, for example, cardiac or esophageal pacing. Such catheters typically have a distal end which includes an instrument, such as a pair of electrodes for cardiac pacing.

In the use of known pacing catheter instruments, the distal end is inserted into a subject orally or nasally, to an approximate depth within the esophagus. The instrument is then positioned by actuating the electrodes and monitoring cardiac condition while adjusting the position of the instrument. Proper positioning of the instrument permits, in the case of a pacing instrument, pacing of the heart using the lowest possible pacing current.

Proper positioning of the instrument, i.e., insertion depth, will, of course, vary between subjects or patients. The depth is, however, generally related to the height of the patient, albeit subject to the variations in each patient's anatomy.

Appropriate positioning of the instrument requires correlating the patient's height to the insertion depth of the instrument. A known technique is to indicate the length of the distal end using a scale which can be read as the instrument is being inserted. Such scales do not take into account patient height and anatomy, and are generally marked in centimeters of length.

Thus, there continues to be a need for an esophageal catheter which is gauged and calibrated to the height of a patient, for proper initial positioning of the catheter.

SUMMARY OF THE INVENTION

A gauging esophageal catheter which is insertable into the esophagus of a subject or patient, has an elongated, flexible body portion having an instrument carried on a distal end. The catheter is insertable into the patient orally or nasally.

The body portion of the catheter has a series of user visible gradations for permitting selective positioning of the instrument at a predetermined insertion depth within the subject. The gradations are calibrated to a parameter, such as the height of the subject, and are read at the mouth or nose.

The gradations may be printed on the body portion. Alternatively, the body portion may have a transparent portion, and the gradations may be carried on a member internal thereto. The gradations are visible through the transparent portion.

The instrument may include conductive electrodes for pacing. The instrument may be implemented as an esophageal stethoscope and carry a perforated distal region for acoustically detecting cardiac or respiratory conditions.

The instrument may be implemented as a nasogastric tube of a type having a distal end extendable into the stomach or intestines of an individual. Alternately, the gradations can be based on correlations with the body weight or surface areas of individuals.

Other features and advantages of the present invention will be apparent from the following detailed description, the accompanying drawings, and the appended claims.

DETAILED DESCRIPTION OF A PREFERRED EMBODIMENT

Figure 1:
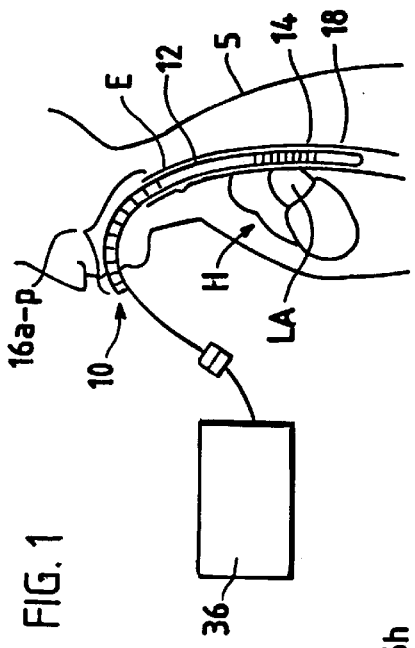
FIG. 1 illustrates a gauging catheter in accordance with the principles of the present invention inserted into the esophagus of an associated subject.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

With reference now to FIG. 1, there is shown a gauging esophageal catheter 10, embodying the principles of the present invention, orally inserted into the esophagus E of an associated subject S. It will be understood by those skilled in the art, that the esophageal catheter 10 can also be nasally inserted into a subject S.

The catheter 10 includes generally, a body portion 12, an instrument 14, and a series of gradations 16a–p along the body portion 12. The instrument is carried on a distal end 18 of the body 12.

The body portion 12 is hollow and is preferably elliptical or round in cross-section. The body 12 is formed of a medical grade material which is sufficiently flexible to permit the body 12 to conform to the bends or deflections of the esophagus E, while having sufficient rigidity to permit unobstructed insertion.

Materials such as polyethylene, and more particularly, high-density polyethylene may be used for such an application. The materials must also be medically appropriate for such a use.

The body includes a series of user visible gradations 16a–p. The gradations 16a–p permit selective positioning of the instrument 14 within the subject S, and are correlated to the height of the subject S. The gradations 16a–p are not, in and of themselves representative of any particular scale. The gradations 16a–p shown on the exemplary catheter 10 of FIG. 2 correlate to patient heights between 40 cm. and 200 cm., 16a and 16p, respectively.

The gradations 16a–p may be printed on the surface 20 of the body 12. Alternatively, the gradations may be carried on a member 22 which extends longitudinally along the interior 23 of the body, which member 22 is visible through a transparent portion 24 of, or window on, the body 12.

The catheter 10 also includes a gripable portion 26, such as a knob or a handle, to manipulate the catheter 10 during insertion and use.

Figure 2:
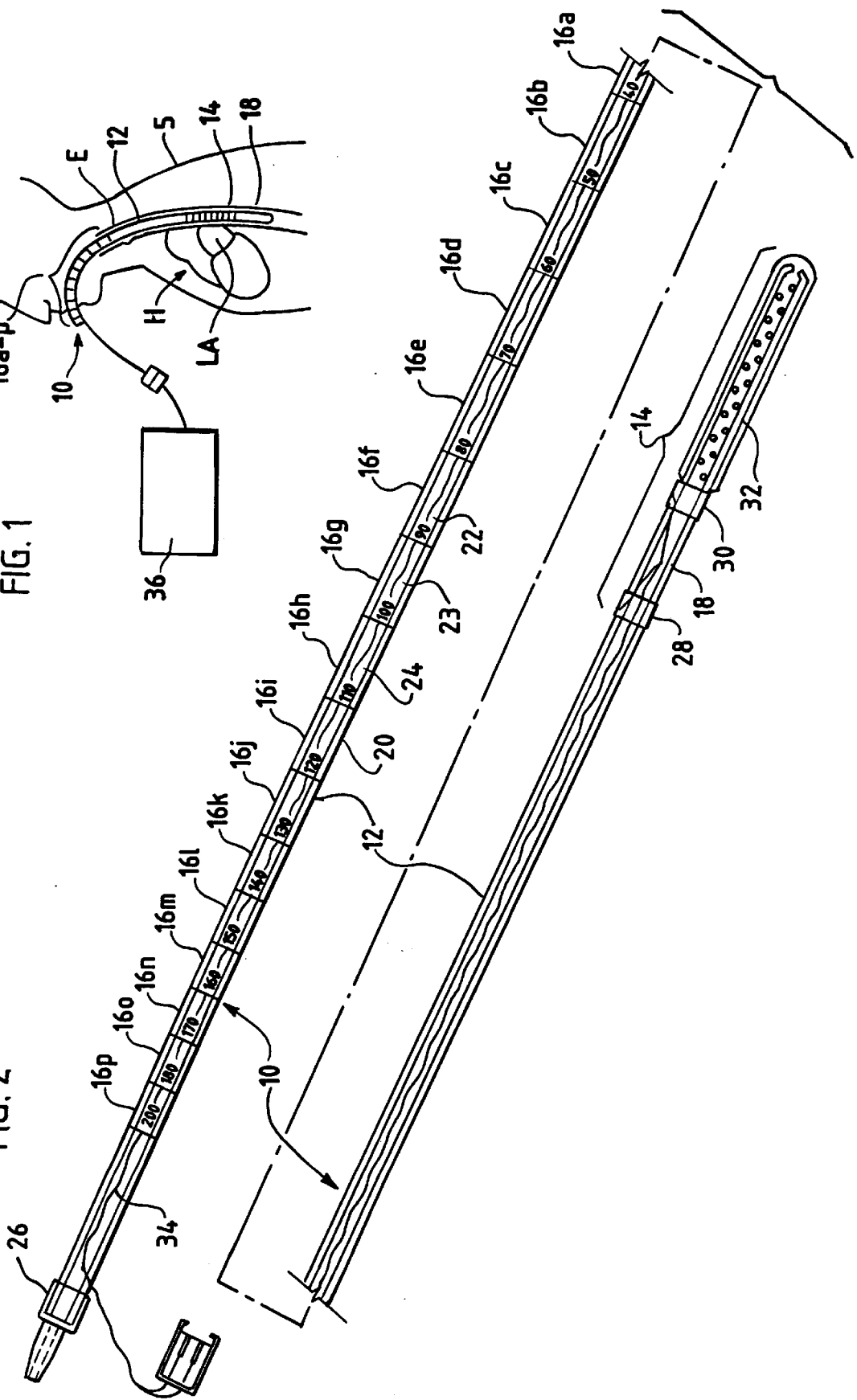
FIG. 2 is a plan view of the esophageal catheter embodying the principles of the present invention, shown in two parts for ease of illustration.

The instrument 14 can be of a type used for esophageal or cardiac pacing. The exemplary instrument 14 shown in FIG. 2 is an esophageal-atrial pacer and stethoscope, and includes first and second spaced apart electrodes 28 and 30. The pacing instrument 14 also includes a perforated region 32 of a known type for acoustically detecting cardiac or respiratory conditions. The instrument 14 may also include one or more sample or pressure measuring ports (not shown).

Examples of such detecting means include acoustic and ultrasonic probes and receivers, such as those disclosed in Metzger et al., U.S. Pat. No. 5,199,433, entitled "Esophageal Recording/Pacing Catheter With Thermistor And Cardiac Imaging Transceiver," which patent is hereby incorporated by reference. The Metzger et al. patent is assigned to the assignee of the present invention.

Conductors 34, such as wires or cables may be routed through the interior 23 of the body 14, and may electrically conduct signals between the electrodes 28 and 30 and a pacing source or monitor 36. The conductors 34 may also electrically conduct signals between the acoustical detection means 32 and the same source or monitor 36, or a separate unit (not shown).

The use of the catheter 10 will be described using the exemplary esophageal-atrial pacing catheter shown in FIG. 2. In the case of such a pacing catheter, it is desirable to position the electrodes 28, 30 behind the left atrium LA of the heart H. This permits successful pacing at the lowest possible pacing current.

In use, first, the height of the subject S or patient is determined. The distal end 18 of the catheter 10 is then inserted orally or nasally into the esophagus E of the subject S.

When used orally, the catheter 10 is inserted into the esophagus E until the gradation which represents the height of the subject S is at the subject's front incisor teeth. When used nasally, the catheter 10 is inserted into the esophagus E until the gradation which represents the height of the subject S is at the subject's nares, i.e., the openings of the nose.

The catheter 10 so positioned, will be initially properly placed. Once initially positioned, the catheter 10 may require slight adjustment, within a range of a few centimeters inward or outward, for optimal functioning. Nevertheless, the catheter of the present invention can be accurately initially positioned within a subject S and require only a small amount of fine adjustment.

For the exemplary esophageal-atrial pacing catheter described, the correlation between insertion depth to the distal electrode 30 and subject height has been experimentally determined as shown in the following Table A.

TABLE A

CORRELATION BETWEEN SUBJECT HEIGHT AND INSERTION DEPTH FOR AN ESOPHAGEAL-ATRIAL PACING CATHETER

| Insertion Depth (cm) | Height (cm) | Insertion Depth (cm) | Height (cm) |
| --- | --- | --- | --- |
| 10 | 40 | 31 | 130 |
| 16 | 60 | 33 | 140 |
| 18 | 70 | 34 | 150 |
| 21 | 80 | 35 | 160 |
| 23 | 90 | 36 | 170 |
| 25 | 100 | 37 | 180 |
| 28 | 110 | 38 | 190 |
| 30 | 120 | 39 | 200 |

It will be understood by those skilled in the art that the present invention can be used to initially position many instruments 14 within a subject S. Such instruments include, for example, all types of esophageal stethoscopes, naso-gastric tubes, pressure measuring catheters, and blood or pressure sampling catheters.

Figure 3:
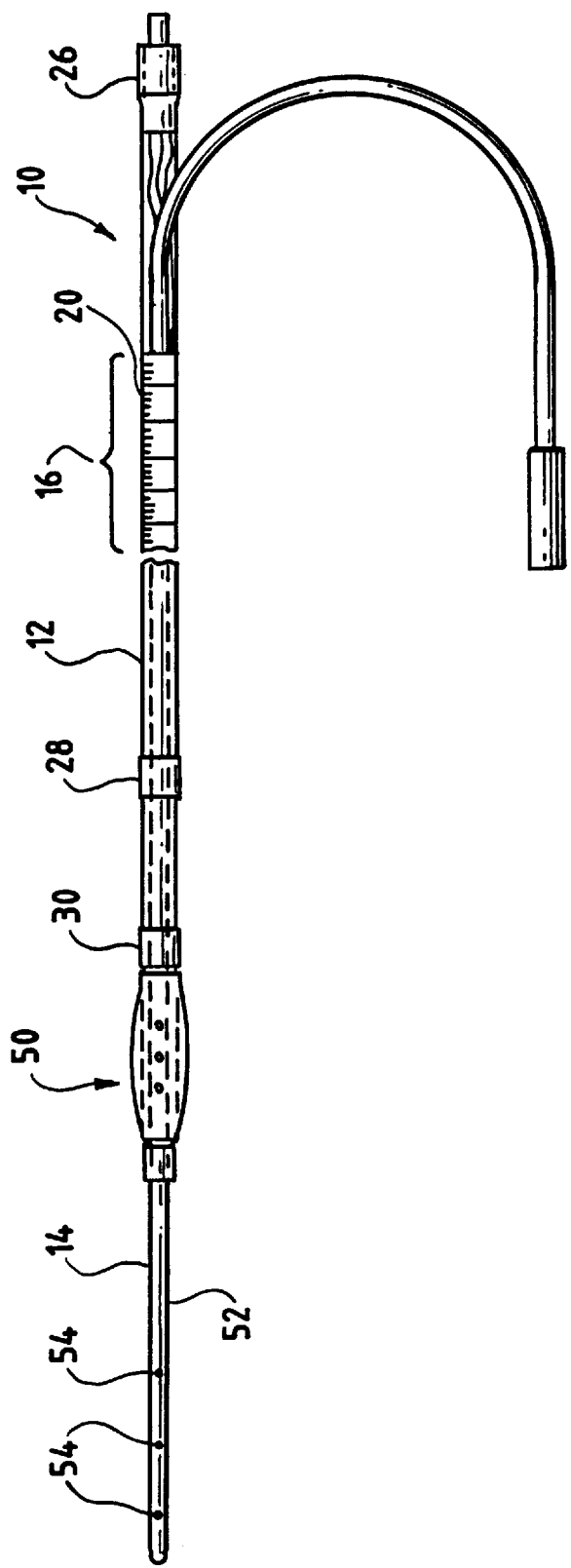
FIG. 3 illustrates a naso-gastric gauging catheter in accordance with the principles of the present invention.

FIG. 3 illustrates an esophageal catheter 10 incorporating a naso-gastric tube 50. The catheter 10 has a body 12 on which the gradations 16 may be carried. The catheter 10 may also include electrodes 28 and 30 thereon.

The naso-gastric tube 50 has a hollow region 52 which has perforations 54 therethrough. The perforations 54 permit evacuation of the contents of the stomach or intestines of a subject.

Although the placement of such instruments within a subject, i.e., insertion depth, may vary among instruments, the initial insertion depth is correlated to the subject's height.

The correlation is experimentally determinable for each type of instrument, for a range of subject heights. As such, for such other types and styles of instruments, different correlations may be required.

It is to be understood that the present invention is not limited to the exemplary instrument and correlations illustrated in the present specification. Correlations based on body surface area or body weight are also within the spirit and scope of the present invention.

From the foregoing it will be observed that numerous modifications and variations can be effectuated without departing from the true spirit and scope of the novel concepts of the present invention. It is to be understood that no limitation with respect to the specific embodiment illustrated is intended or should be inferred. The disclosure is intended to cover by the appended claims all such modifications as fall within the scope of the claims.

What is claimed is:

1. A gauging esophageal catheter insertable into an esophagus of an associated subject, the subject having a determinable height, the esophageal catheter comprising:

an elongated, flexible body portion having a proximal end and a distal end, said flexible body portion being insertable at least partially orally or nasally, said distal end being insertable into the esophagus of the subject;

an instrument carried on said distal end; and said body portion having a series of user visible gradations for permitting selective positioning of said distal end at a predetermined insertion depth within the subject, said gradations being calibrated according to subject height and said gradations labeled in measurements corresponding to subject height in accordance with oral or nasal insertion.

2. The gauging esophageal catheter as claimed in claim 1, said gradations being printed on said body portion.

3. The gauging esophageal catheter as claimed in claim 1 wherein a portion of said body portion is transparent, and including a longitudinally extending member internal thereto, said member carrying said gradations thereon.

4. The gauging esophageal catheter as claimed in claim 1, wherein said instrument includes conductive electrodes for pacing.

5. The gauging esophageal catheter as claimed in claim 1, wherein said instrument is selected from a group including at least one pacing electrode, an acoustic input port and an echocardiography transmitter.

6. The gauging esophageal catheter as claimed in claim 1, said gradations being calibrated to the height of the subject in a range of about 40 cm. to about 200 cm., and the associated predetermined insertion depth within the subject.

7. The gauging esophageal catheter as claimed in claim 1, wherein said instrument includes first and second spaced apart electrodes and an acoustic input port for detecting cardiac or respiratory sounds.

8. The gauging esophageal catheter as claimed in claim 1 wherein said gradations are calibrated based on one of weight and body surface area of the subject.

9. The gauging esophageal catheter as claimed in claim 1 wherein said instrument includes two or more monitoring or pacing electrodes.

10. The gauging esophageal catheter as claimed in claim 1 wherein said body portion is formed at least in part as a naso-gastric tube with a distal end insertable at least into a stomach of the subject.

11. A gauging catheter insertable into an esophagus of an associated patient wherein the patient has a predetermined height, the catheter comprising:

an elongated, tubular, flexible body portion for insertion into one of a patient's mouth or nose, and having a proximal and a distal end, said distal end being insertable, at least, into the esophagus of the patient; and a plurality of user-visible patient height indicators carried on the proximal end of the body portion for permitting selective positioning of the distal end at a predetermined insertion depth within the patient wherein the visible indicators are calibrated according to a range of heights and marked in measuring units corresponding to patient heights.

12. A catheter as in claim 11 which includes an instrument carried on the distal end.

13. A catheter as in claim 12 wherein the instrument includes at least one conductive electrode suitable for cardiac pacing.

14. A gauging esophageal catheter insertable into an esophagus of an associated subject, the subject having a determinable height, the esophageal catheter comprising:

an elongated, flexible body portion having a proximal end and a distal end, said flexible body portion being insertable at least partially into a subject's mouth or nose, said distal end being insertable into the esophagus of the subject;

said body portion having a series of user visible gradations, said series of gradations at least partially insertable into the subject's mouth or nose for permitting selective positioning of said distal end at a predetermined insertion depth within the subject, said gradations indicative of subject height and being calibrated according to subject height, and said series of gradations read at either the subject's teeth or nares.

15. The gauging esophageal catheter as claimed in claim 14, said gradations being printed on said body portion.

16. The gauging esophageal catheter as claimed in claim 14 wherein a portion of said body portion is transparent, and including a longitudinally extending member internal thereto, said member carrying said gradations thereon.

17. The gauging esophageal catheter as claimed in claim 14 further comprising an instrument carried on said distal end, wherein said instrument includes conductive electrodes for pacing.

18. The gauging esophageal catheter as claimed in claim 17, further comprising an instrument carried on said distal end, wherein said instrument is selected from a group including at least one pacing electrode, an acoustic input port and an echocardiography transmitter.

19. The gauging esophageal catheter as claimed in claim 14, further comprising an instrument carried on said distal end, said gradations being calibrated to the height of the subject in a range of about 40 cm. to 200 cm., and the associated predetermined insertion depth within the subject.

20. The gauging esophageal catheter as claimed in claim 14, further comprising an instrument carried on said distal end, wherein said instrument includes first and second spaced apart electrodes and an acoustic input port for detecting cardiac or respiratory sounds.

21. The gauging esophageal catheter as claimed in claim 14 wherein said instrument includes two or more monitoring or pacing electrodes.

22. The gauging esophageal catheter as claimed in claim 14 wherein said body portion is formed at least in part as a naso-gastric tube with a distal end insertable at least into a stomach of the subject.

* * * * *